(12) United States Patent
Chapman et al.

(10) Patent No.: US 11,497,793 B2
(45) Date of Patent: Nov. 15, 2022

(54) COMPOSITIONS AND METHODS FOR TREATING GLIOBLASTOMA

(71) Applicant: TEL HASHOMER MEDICAL RESEARCH INFRASTRUCTURE AND SERVICES LTD., Ramat Gan (IL)

(72) Inventors: Joab Chapman, Kiryat Ono (IL); Efrat Shavit-Stein, Karkur (IL)

(73) Assignee: TEL HASHOMER MEDICAL RESEARCH INFRASTRUCTURE AND SERVICES LTD., Ramat Gan (IL)

( * ) Notice: Subject to any disclaimer, the term of this patent is extended or adjusted under 35 U.S.C. 154(b) by 64 days.

(21) Appl. No.: 17/050,910

(22) PCT Filed: Apr. 16, 2019

(86) PCT No.: PCT/IL2019/050430
§ 371 (c)(1),
(2) Date: Oct. 27, 2020

(87) PCT Pub. No.: WO2019/211829
PCT Pub. Date: Nov. 7, 2019

(65) Prior Publication Data
US 2021/0228681 A1    Jul. 29, 2021

Related U.S. Application Data

(60) Provisional application No. 62/665,531, filed on May 2, 2018.

(51) Int. Cl.
| | |
|---|---|
| *A61K 38/17* | (2006.01) |
| *A61K 47/64* | (2017.01) |
| *A61P 35/00* | (2006.01) |
| *A61K 31/495* | (2006.01) |
| *A61K 38/06* | (2006.01) |
| *A61K 38/08* | (2019.01) |

(52) U.S. Cl.
CPC .......... *A61K 38/177* (2013.01); *A61K 31/495* (2013.01); *A61K 38/06* (2013.01); *A61K 38/08* (2013.01); *A61K 47/646* (2017.08); *A61P 35/00* (2018.01)

(58) Field of Classification Search
None
See application file for complete search history.

(56) References Cited

U.S. PATENT DOCUMENTS

| 4,161,522 A | 7/1979 | Hamburger |
|---|---|---|
| 4,966,848 A | 10/1990 | Smith et al. |
| 5,223,421 A | 6/1993 | Smith et al. |
| 5,837,218 A | 11/1998 | Peers et al. |
| 7,842,716 B2 | 11/2010 | Serebruany |
| 8,232,295 B2 | 7/2012 | Serebruany |
| 9,180,163 B2 | 11/2015 | Tsopanoglu et al. |
| 2004/0092535 A1 | 5/2004 | Barsanti |
| 2007/0142272 A1 | 6/2007 | Zlokovic |
| 2007/0219154 A1 | 9/2007 | Liu et al. |
| 2009/0176803 A1 | 7/2009 | Perez |
| 2009/0281100 A1 | 11/2009 | Barsanti |
| 2010/0129470 A1* | 5/2010 | Laughlin .................. A61P 35/00 514/249 |
| 2010/0247440 A1 | 9/2010 | Morton |
| 2012/0232097 A1 | 9/2012 | Perez |
| 2014/0288115 A1 | 9/2014 | Chen et al. |

FOREIGN PATENT DOCUMENTS

| WO | 02071847 A1 | 9/2002 | |
|---|---|---|---|
| WO | 2013070256 A2 | 5/2013 | |
| WO | 2013173676 A1 | 11/2013 | |
| WO | 2015173802 A1 | 11/2015 | |
| WO | WO-2015173802 A1 * | 11/2015 | ......... A61K 38/1796 |
| WO | 2016061231 A1 | 4/2016 | |

OTHER PUBLICATIONS

McRedmond et al (2000) Streptokinase-induced platelet activation involves antistreptokinase antibodies and cleavage of protease-activated receptor-1, Blood 95(4): 1301-8.
Zania et al (2009) Parstatin, the Cleaved Peptide on Proteinase-Activated Receptor 1 Activation, Is a Potent Inhibitor of Angiogenesis, Journal of Pharmacology and Experimental Therapeutics, 328(2): 378-389.
PCT Search Report for International Application No. PCT/IL2019/050430 dated Oct. 11, 2019, 5 pp.
PCT Written Opinion for International Application No. PCT/IL2019/050430 dated Oct. 11, 2019, 9 pp.
PCT Preliminary Report on Patentability for International Application No. PCT/IL2019/050430, dated Nov. 3, 2020, 10 pp.
Mihara et al., (2013) Neutrophil elastase and proteinase-3 trigger G protein-biased signaling through proteinase-activated receptor-1 (PAR1). Journal of Biological Chemistry, 288(46), 32979-32990.
Shavit et al., (2008) Thrombin receptor PAR-1 on myelin at the node of Ranvier: a new anatomy and physiology of conduction block. Brain, 131(4), 1113-1122.
Shavit et al., (2011) Anatomical localization of protease-activated receptor-1 and protease-mediated neuroglilal crosstalk on peri-synaptic astrocytic endfeet. Journal of neurochemistry, 119(3), 460-473.
PCT Search Report for International Application No. PCT/IL2015/050488 dated Aug. 27, 2015, 6 pp.
PCT Written Opinion for International Application No. PCT/IL2015/050488 dated Aug. 27, 2015, 7 pp.
PCT Preliminary Report on Patentability for International Application No. PCT/IL2015/050488 dated Nov. 15, 2016, 8 pp.

* cited by examiner

*Primary Examiner* — Christina Bradley
(74) *Attorney, Agent, or Firm* — The Roy Gross Law Firm, LLC; Roy Gross (57) ABSTRACT

Compositions and methods for treating malignant gliomas such as glioblastoma are provided, comprising a combination of a peptide conjugate comprising an amino acid sequence derived from the N-terminus of the receptor PAR-1, and the chemotherapeutic agent temozolomide.

20 Claims, 4 Drawing Sheets

Specification includes a Sequence Listing.

COMPOSITIONS AND METHODS FOR TREATING GLIOBLASTOMA

CROSS REFERENCE TO RELATED APPLICATIONS

This application is a National Phase of PCT Patent Application No. PCT/IL2019/050430 having International filing date of Apr. 16, 2019, which claims the benefit of priority of U.S. Provisional Application No. 62/665,531 filed on May 2, 2018 entitled COMPOSITIONS AND METHODS FOR TREATING GLIOBLASTOMA. The contents of the above applications are all incorporated by reference as if fully set forth herein in their entirety.

FIELD OF THE INVENTION

The present invention relates to a combined therapy for glioblastoma. In particular, the present invention relates to a combination of a peptide conjugate derived from the N-terminus of PAR-1, a receptor involved in glioma proliferation, and chemotherapy in the treatment of glioblastoma.

BACKGROUND OF THE INVENTION

Glioblastoma multiforme (GBM or simply "glioblastoma") is the most common and most aggressive of malignant primary brain tumors in adults and is one of a group of tumors referred to as gliomas (tumors originating from glial cells). Classified as a Grade IV astrocytoma, GBM develops from astrocytes, the star-shaped glial cells that support nerve cells. GBM develops primarily in the cerebral hemispheres but can develop in other parts of the brain, brainstem, or spinal cord.

GBM is characterized by rapid cell proliferation and marked propensity to invade and damage the surrounding normal brain tissue, rendering the complete surgical removal impossible. Despite available treatments, including surgical resection, chemotherapy and radiotherapy, the vast majority of patients exhibit a poor median survival of less than 15 months following diagnosis. Therefore, the development of novel therapeutic approaches to treat GBM remains of critical importance.

WO 2015/173802, to the assignee of the present invention, discloses a peptide conjugate comprising an alpha-amino protecting moiety, a peptide comprising the amino acid sequence at least 3 amino-acid long derived from the N-terminus of PAR-1, or an active variant thereof, and a protease-disabling moiety. Among other peptide conjugates, the conjugate tosyl-ATLDPR-chloromethylketone is disclosed. WO 2015/173802 further discloses the use of the peptide conjugates in the treatment of diseases or disorders associated with excessive protease receptor activity, including, glioma, astrocytoma, cancer, solid tumor, brain tumor, glioblastoma, oligodendroglioma, ependymoma, mixed gliomas and glioblastoma multiforme.

Despite the extensive efforts made so far, the median survival time of GBM patients is still very poor, in part due to the lack of adequate therapeutic options. There remains a need for more effective treatments for malignant brain tumors such as GBM.

SUMMARY OF THE INVENTION

The present invention provides according to some aspects combined therapies for malignant gliomas, particularly glioblastoma, using a peptide conjugate derived from the N-terminus of PAR-1, a receptor involved in glioma proliferation, and the chemotherapeutic agent temozolomide. In particular embodiments, the combined therapies disclosed herein utilize a peptide conjugate comprising 3-20 amino acids from the N-terminus of PAR-1 conjugated to an alpha-amino protecting moiety and a protease-disabling moiety, in combination with temozolomide.

The present invention is based in part on the surprising synergistic effect of a combination of the peptide conjugate tosyl-Ala-Thr-Leu-Asp-Pro-Arg-chloromethylketone (tosyl-SEQ ID NO: 3-chloromethylketone), termed herein "SIXAC", and temozolomide (TMZ) in reducing proliferation of glioma cells in vitro, and the significant improvement in survival obtained by this combination in an in vivo model of glioblastoma, even for high grade tumors. It was surprisingly found that a major inhibitory effect on proliferation of glioma cells is achieved with a combination of SIXAC and TMZ, at concentrations in which TMZ alone is ineffective and the peptide alone results only in a minor effect. Treatment with the combination in effect transformed cancer cells that are essentially resistant to TMZ into cancer cells that are responsive to TMZ, and the result is a pronounced effect on proliferation of the cancer cells.

The present invention therefore provides a more effective treatment for malignant gliomas such as glioblastoma.

According to one aspect, the present invention provides a method for treating glioblastoma in a subject in need thereof, the method comprising administering to the subject a peptide conjugate having the following general formula:

α-amino protecting moiety-PAR-1 peptide-protease-disabling moiety, wherein the PAR-1 peptide is selected from the group consisting of Asp-Pro-Arg and SEQ ID NOs: 1-17, and administering temozolomide the said subject.

In some embodiments, the PAR-1 peptide is selected from the group consisting of Asp-Pro-Arg and SEQ ID NOs: 1-4.

In some embodiments, the PAR-1 peptide is Ala-Thr-Leu-Asp-Pro-Arg (SEQ ID NO: 3).

In some embodiments, the α-amino protecting moiety is tosyl or a derivative thereof.

In some embodiments, the protease-disabling moiety is chloromethylketone or a derivative thereof.

In some embodiments, the peptide conjugate is: tosyl-Ala-Thr-Leu-Asp-Pro-Arg-chloromethylketone (tosyl-SEQ ID NO: 3-chloromtethylketone).

In some embodiments, the peptide conjugate is administered into the central nervous system (CNS) of the subject. In some embodiments, the peptide conjugate is administered into the CNS of the subject by intracerebroventricular (ICV) administration.

In some embodiments, the peptide conjugate is administered systemically. In some embodiments, the peptide conjugate is administered via intravenous or subcutaneous administration.

In some embodiments, the peptide conjugate is administered once daily to once weekly.

In some embodiments, the temozolomide is administered orally. In additional embodiments, the temozolomide is administered by intravenous infusion.

In some embodiments, the subject is further receiving radiotherapy.

In some embodiments, the peptide conjugate and the temozolomide are administered on the same day. In other embodiments, the peptide conjugate and the temozolomide are administered on separate days.

In some embodiments, the peptide conjugate and the temozolomide are administered concomitantly in a plurality of treatment cycles over a period of time of 1-12 months, wherein each treatment cycle comprises concomitant administration of the peptide conjugate and temozolomide for a predetermined period of time followed by a period of time in which the peptide conjugate and temozolomide are not administered.

In some embodiments, the temozolomide is administered in treatment cycles, each comprising a predetermined period of time in which the temozolomide is administered followed by a period of time in which the temozolomide is not administered, and the peptide conjugate is administered continuously.

In some embodiments, the peptide conjugate is administered directly into the tumor. In other embodiments, the peptide conjugate is administered into an area from which the tumor or a portion thereof has been surgically resected. In additional embodiments, the peptide conjugate is administered into an area surrounding the tumor.

According to another aspect, the present invention provides a method for treating a malignant glioma in a subject in need thereof, the method comprising administering to the subject a peptide conjugate having the following general formula:

α-amino protecting moiety-PAR-1 peptide-protease-disabling moiety,
wherein the PAR-1 peptide is selected from the group consisting of Asp-Pro-Arg and SEQ ID NOs: 1-17,
and administering temozolomide the said subject.

In some embodiments, the malignant glioma is glioblastoma multiforme.

According to yet another aspect, the present invention provides a pharmaceutical composition comprising a peptide conjugate having the following general formula:

α-amino protecting moiety-PAR-1 peptide-protease-disabling moiety,
wherein the PAR-1 peptide is selected from the group consisting of Asp-Pro-Arg and SEQ ID NOs: 1-17,
for use in the treatment of a malignant glioma in a subject in combination with temozolomide.

In some embodiments, the malignant glioma is glioblastoma multiforme.

These and further aspects and features of the present invention will become apparent from the detailed description, examples and claims which follow.

DETAILED DESCRIPTION OF THE INVENTION

The present invention provides according to some aspects methods for treating malignant brain tumors, particularly malignant gliomas such as glioblastoma multiforme. The methods of the present invention utilize a combination of a peptide conjugate comprising a sequence derived from the N-terminus of PAR-1 and the chemotherapeutic agent temozolomide (TMZ). The combination was found to have a synergistic effect in reducing proliferation of glioma cells, and to be highly effective in improving survival in a rat model of glioblastoma, as exemplified herein below.

Gliomas are tumors developing from glial cells in the brain or spinal cord, which may be benign or malignant. Three types of glial cells can produce tumors, namely, astrocytes (astrocytomas), ependymal cells (ependymomas) and oligodendrocytes (oligodendrogliomas). Astrocytomas are graded 1-4 according to the aggressiveness of the tumor, where grades 1-2 are considered benign, and grades 3-4, called anaplastic astrocytoma and glioblastoma multiforme, respectively, are considered malignant.

According to an aspect of the present invention, a method for treating glioblastoma multiforme in a subject in need thereof is provided, comprising administering to the subject a peptide conjugate as described herein and temozolomide. In some embodiments, a method for treating glioblastoma multiforme in a subject in need thereof is provided, comprising administering a peptide conjugate as described herein into the central nervous system (CNS) of the subject, and administering temozolomide to said subject. In other embodiments, a method for treating glioblastoma multiforme in a subject in need thereof is provided, comprising systemically administering to the subject a peptide conjugate as described herein in combination with temozolomide.

According to another aspect of the present invention, a method for treating a malignant glioma in a subject in need thereof is provided, comprising administering a peptide conjugate as described herein to the subject, for example, into the CNS of the subject, and administering temozolomide to said subject.

According to an additional aspect, a peptide conjugate as described herein and temozolomide are provided, for use in treating a malignant glioma in a subject, particularly for use in treating glioblastoma multiforme.

According to an additional aspect, a pharmaceutical composition comprising a peptide conjugate as described herein and a pharmaceutical composition comprising temozolomide are provided, for combined use in treating a malignant glioma, particularly for use in treating glioblastoma multiforme.

According to an additional aspect, there is provided a pharmaceutical composition comprising a peptide conjugate as described herein, for use in the treatment of a malignant glioma in a subject in combination with temozolomide, particularly for use in the treatment of glioblastoma multiforme.

According to an additional aspect, the use of a peptide conjugate as described herein is provided, for the preparation of medicament for the treatment of a malignant glioma in combination with temozolomide, particularly for the treatment of glioblastoma multiforme.

In some embodiments, the peptide conjugate is administered into the CNS of the subject and the temozolomide is administered systemically, for example via oral or intravenous administration.

In other embodiments, the peptide conjugate is administered systemically, for example, via intravenous or subcutaneous administration, and the temozolomide is administered systemically, for example via oral or intravenous administration.

In some embodiments, the malignant glioma is glioblastoma multiforme (grade 4 astrocytoma). In other embodiments, the malignant glioma is anaplastic astrocytoma (grade 3 astrocytoma).

As used herein, "treating" and "treatment" include any one or more of inhibiting the progression of the disease, attenuating the progression of the disease and preventing deterioration of the disease, including for example reducing tumor size, attenuating or preventing tumor growth, and reducing symptoms associated with the presence of the tumor. "Treating" and "treatment" also encompass prolonging survival of a subject beyond that expected in the absence of treatment.

Subjects in need of treatment according to the present invention are typically human subjects afflicted with a malignant glioma such as glioblastoma. In some embodiments, subjects in need of treatment particularly include subjects afflicted with a malignant brain tumor that expresses or over-expresses PAR-1. The tumor may be a primary tumor, a secondary tumor, or a recurrent tumor. Each possibility represents a separate embodiment of the present invention.

The peptide conjugate and temozolomide are typically administered to subjects in need thereof as pharmaceutical compositions/formulations. A "pharmaceutical composition" typically contains the therapeutic agent mixed with auxiliary substances that facilitate its delivery, such as pharmaceutically acceptable concentrations of one or more of: salt(s), buffering agent(s), preservative(s) and various compatible carrier(s). For all forms of delivery, the therapeutic agent may be formulated in a salt solution, preferably at a pH lower than physiological pH.

The pharmaceutical compositions may be prepared by known methods for the preparation of pharmaceutically acceptable compositions suitable for administration to subjects, such that an effective quantity of the therapeutic is combined in a mixture with the auxiliary substances. Depending on the intended mode of administration and the intended use, the compositions may be in the form of solid, semi-solid, or liquid dosage forms, such as, for example, tablets, capsules, solutions, powders, granules, crystals, liquids, suspensions, liposomes, nano-particles, nano-emulsions, etc.

The peptide conjugate and temozolomide are used according to the present invention in therapeutically effective amounts. As used herein, a "therapeutically effective amount" indicates an amount of a compound expected to be effective to treat the disease, as defined above. Determination of a therapeutically effective amount is well within the capability of those skilled in the art, especially in light of the detailed disclosure and Examples provided herein.

Dosage of the therapeutic agents will depend on, among other things, the condition of the subject, the particular type of tumor being treated, and the route of administration.

Temozolomide (TMZ) is an alkylating agent approved for use in the treatment of patients with malignant gliomas, such as glioblastoma multiforme or anaplastic astrocytoma. As used herein, "temozolomide" also encompasses pharmaceutically acceptable salts of temozolomide.

TMZ is approved for use as a monotherapy and also in combination with focal radiotherapy. In patients with newly-diagnosed glioblastoma multiforme, TMZ is typically administered in combination with focal radiotherapy (concomitant phase) followed by up to 6 cycles of TMZ monotherapy (monotherapy phase).

In the concomitant phase, TMZ is typically administered daily for several weeks concomitant with focal radiotherapy, for example, administered orally at a dose of 75 mg/m2 daily for 42 days concomitant with focal radiotherapy (60 Gy administered in 30 fractions).

In the monotherapy phase, TMZ is typically administered for up to 6 treatment cycles, each cycle composed of 28 days. Dose in Cycle 1 is typically 150 mg/m2 once daily for 5 days followed by 23 days without treatment. At the start of Cycle 2, the dose is escalated to 200 mg/m2 if the patient's condition permits. If escalated, the dose remains at 200 mg/m2 per day for the first 5 days of each cycle except if toxicity occurs.

TMZ is commercially available as hard capsules for oral administration containing 5 mg, 20 mg, 100 mg, 140 mg, 180 mg or 250 mg temozolomide, and as a 2.5 mg/ml powder for solution for infusion, for administration by intravenous infusion.

In some embodiments, administration of TMZ according to the present invention is carried out according to known treatment protocols.

In some embodiments, the combination therapy disclosed herein employs the use of doses of TMZ that are lower than those commonly used or approved for human therapy. In some embodiments, the combination therapy disclosed herein employs the use of doses of TMZ that are at least 5%, 10%, 20%, 30%, 40%, 50%, 60%, 70%, 80% or 90% lower than those commonly used or approved for use for human therapy. Each possibility represents a separate embodiment of the present invention.

In some embodiments, the subject receiving treatment according to the present invention also receives concomitant radiotherapy. In some embodiments, the methods of the present invention further comprise administering radiotherapy. Radiotherapy is typically administered in a series of sessions, over a period of several weeks. For example, the radiotherapy may be administered 3, 4, 5, 6 or 7 days a week, over a period of four, five, six or seven weeks.

Peptide Conjugate

The peptide conjugate of the present invention is derived from the N-terminus of PAR-1. Protease activated receptors (PARs) are a family of four G protein coupled receptors numbered PAR-1 to PAR-4. Since its discovery in the early 90's, PAR-1 has been found in many tissues including the brain where it is found on several cell types including neurons, astrocytes and microglia. PAR-1 is activated, inter alia, by the protease thrombin, which recognizes PAR-1 at a specific location within the N-terminus of PAR-1 and cleaves a portion of PAR-1 ectodomain.

PAR-1 was found to be highly expressed by glioma cells, and to play a role in glioma proliferation and survival. The inventors of the present invention have previously shown that PAR-1 blocking by specific antagonists caused a significant decrease in glioma proliferation. In addition, the inventors of the present invention designed peptide conjugates derived from the N-terminus sequence of PAR-1 that is recognized by thrombin, as a decoy for thrombin to prevent its binding to, and subsequent cleavage and activation of, PAR-1 (see WO 2015/173802). The inventors of the present invention have shown that the peptide conjugates inhibit thrombin activity, inhibit proliferation of glioma cells, induce reduction in glioblastoma multiforme (GBM) tumors in vivo and reduce formation of edema associated with GBM. Advantageously, the peptide conjugates were found to exert the aforementioned activities at particularly low concentrations, within the range of nanomolars in vitro and micromolars in vivo. The activity of the peptide conjugates is performed without negatively affecting blood coagulation (see WO 2015/173802). Without being bound by any particular theory of a mechanism of action, it is contemplated that the peptide conjugates reduce PAR-1 activation, and consequently reduce proliferation of glioma cells expressing PAR-1.

The peptide conjugate utilized in the present invention comprises an alpha-amino protecting moiety, an amino acid sequence derived from the N-terminus of PAR-1, and a protease-disabling moiety.

In particular, a peptide conjugate for use according to the present invention has the following general formula:
  alpha-amino protecting moiety-PAR-1 peptide-protease disabling moiety,
  wherein the PAR-1 peptide is selected from the group consisting of Asp-Pro-Arg and SEQ ID NOs: 1-17.

In some embodiments, a peptide conjugate for use according to the present invention comprises:
  an alpha-amino protecting moiety,
  a peptide consisting of the amino acid sequence selected from the group of Asp-Pro-Arg and SEQ ID NOs: 1-17, and
  a protease-disabling moiety,
  wherein the peptide is bound to the alpha-amino protecting moiety and to the protease-disabling moiety, wherein the protease-disabling moiety is chloromethylketone or derivatives thereof and wherein the alpha-amino protecting moiety is tosyl or derivatives thereof.

In some embodiments, the PAR-1 peptide is Asp-Pro-Arg. In some embodiments, the PAR-1 peptide is the peptide set forth as SEQ ID NO: 1. In some embodiments, the PAR-1 peptide is the peptide set forth as SEQ ID NO: 2. In some embodiments, the PAR-1 peptide is the peptide set forth as SEQ ID NO: 3. In some embodiments, the PAR-1 peptide is the peptide set forth as SEQ ID NO: 4. In some embodiments, the PAR-1 peptide is the peptide set forth as SEQ ID NO: 5. In some embodiments, the PAR-1 peptide is the peptide set forth as SEQ ID NO: 6. In some embodiments, the PAR-1 peptide is the peptide set forth as SEQ ID NO: 7. In some embodiments, the PAR-1 peptide is the peptide set forth as SEQ ID NO: 8. In some embodiments, the PAR-1 peptide is the peptide set forth as SEQ ID NO: 9. In some embodiments, the PAR-1 peptide is the peptide set forth as SEQ ID NO: 10. In some embodiments, the PAR-1 peptide is the peptide set forth as SEQ ID NO: 11. In some embodiments, the PAR-1 peptide is the peptide set forth as SEQ ID NO: 12. In some embodiments, the PAR-1 peptide is the peptide set forth as SEQ ID NO: 13. In some embodiments, the PAR-1 peptide is the peptide set forth as SEQ ID NO: 14. In some embodiments, the PAR-1 peptide is the peptide set forth as SEQ ID NO: 15. In some embodiments, the PAR-1 peptide is the peptide set forth as SEQ ID NO: 16. In some embodiments, the PAR-1 peptide is the peptide set forth as SEQ ID NO: 17.

| Amino-acid sequences of peptide moieties. | |
|---|---|
| SEQ ID | Amino-acid sequence |
| — | DPR |
| SEQ ID NO: 1 | LDPR |
| SEQ ID NO: 2 | TLDPR |
| SEQ ID NO: 3 | ATLDPR |
| SEQ ID NO: 4 | NATLDPR |
| SEQ ID NO: 5 | TNATLDPR |
| SEQ ID NO: 6 | ATNATLDPR |
| SEQ ID NO: 7 | KATNATLDPR |
| SEQ ID NO: 8 | SKATNATLDPR |
| SEQ ID NO: 9 | ESKATNATLDPR |
| SEQ ID NO: 10 | PESKATNATLDPR |
| SEQ ID NO: 11 | RPESKATNATLDPR |
| SEQ ID NO: 12 | RRPESKATNATLDPR |
| SEQ ID NO: 13 | ARRPESKATNATLDPR |
| SEQ ID NO: 14 | RARRPESKATNATLDPR |
| SEQ ID NO: 15 | TRARRPESKATNATLDPR |
| SEQ ID NO: 16 | RTRARRPESKATNATLDPR |
| SEQ ID NO: 17 | ARTRARRPESKATNATLDPR |

The sequence Asp-Pro-Arg corresponds to amino acids 39-41 of the human PAR-1 (Accession no. NP_001983.2). SEQ ID NO: 1 corresponds to amino acids 38-41 of the human PAR-1. Accordingly, SEQ ID NOs: 2-17 correspond to amino acids 37-41, 36-41, 35-41 and so forth up to amino acids 22-41 of the human PAR-1.

In some particular embodiments, the PAR-1 peptide is ATLDPR (SEQ ID NO: 3). In additional embodiments, the PAR-1 peptide comprises ATLDPR (SEQ ID NO: 3).

In some particular embodiments, a peptide conjugate for use according to the present invention has the following general formula:
alpha-amino protecting moiety-ATLDPR-protease-disabling moiety (alpha-amino protecting moiety-SEQ ID NO: 3-protease-disabling moiety).

The term "alpha-amino protecting moiety" refers to any moiety attached to the amino terminal of the peptide that is capable of protecting the peptide conjugate from adverse effects such as proteolysis, degradation or clearance, or alleviating such adverse effects.

In some embodiments, the alpha-amino protecting moiety is tosyl ($CH_3C_6H_4SO_2$) (a tosyl group) or derivatives thereof.

Additional alpha-amino protecting moieties that may be used include t-butyloxycarbonyl (BOC, $(CH_3)_3COCO-$, t-BOC), t-amyloxycarbonyl, adamantyl-oxycarbonyl, and p-methoxybenzyloxycarbonyl, 9-fluorenylmethoxycarbonyl (FMOC), 2-chlorobenzyloxycarbonyl, nitro, benzyloxycarbonyl (CBZ), 2,2,5,7,8-pentamethylchroman-6-sulfonyl, 2,3,6-trimethyl-4-methoxyphenylsulfonyl, t-butyl benzyl (BZL) or substituted BZL, such as, p-methoxybenzyl, p-nitrobenzyl, p-chlorobenzyl, o-chlorobenzyl, and 2,6-dichlorobenzyl, t-butyl, cyclohexyl, cyclopentyl, benzyloxymethyl (BOM), tetrahydropyranyl, trityl, chlorobenzyl, 4-bromobenzyl, and 2,6-dichlorobenzyl. Each possibility represents a separate embodiment of the present invention.

The term "protease-disabling moiety" refers to any moiety capable of binding to a protease and transiently or permanently disabling its proteolytic activity. In particular, the protease-disabling moiety of the peptide conjugates of the present invention is a thrombin-disabling moiety. In some embodiments, the protease disabling moiety is a thrombin inhibitor.

In some particular embodiments, the protease disabling moiety is chloromethylketone (—COCH$_2$Cl) (CMK) or a derivative thereof.

Additional protease disabling moieties that may be used include: irreversible inhibitors such as substituted acetyl (1-x-actyl), sulfonylfluorides (SO$_2$F), esters (—COOR), and boronic acids (—B(OR)$_2$); reversible inhibitors such as aldehydes (—CHO), arylketones (—CO-Aryl), trifluoromethylketones (—COCF$_3$) and ketocarboxylic acids (—CO-COOH).

In some embodiments, the protease-disabling moiety may be a substituted acetyl. In some embodiments, the substituted acetyl may be haloacetyl. In some embodiments, the haloacetyl may be chloroacetyl. In some embodiments, the protease-disabling moiety may be chloromethylketone (CMK).

In some embodiments, the alpha-amino protecting moiety is tosyl or a derivative thereof. In some embodiments, the protease-disabling moiety is chloromethylketone (CMK) or a derivative thereof.

In some particular embodiments, the peptide conjugate for use according to the present invention is: Tosyl-ATLDPR-CMK (tosyl-SEQ ID NO: 3-chloromethylketone).

In some embodiments, the peptide conjugate has the general formula:
alpha-amino protecting moiety-PAR-1 peptide-protease-disabling moiety,
wherein:
the alpha-amino protecting moiety is tosyl or a derivative thereof;
the PAR-1 peptide is selected from the group consisting of Asp-Pro-Arg and SEQ ID NOs: 1-17; and
the protease-disabling moiety is CMK or a derivative thereof.

In some embodiments, the peptide conjugate has a structure according to the following formula:
Tosyl-PAR-1 peptide-CMK, wherein the PAR-1 peptide is selected from the group consisting of Asp-Pro-Arg and SEQ ID NOs: 1-17.

In some particular embodiments, the peptide conjugate is tosyl-ATLDPR-CMK (tosyl-SEQ ID NO: 3-CMK).

The C' terminal amino acid of the PAR-1 peptide may covalently bind to the protease-disabling moiety directly or via a linker, through its C' carboxyl-group or through its side-chain. Each possibility represents a separate embodiment of the present invention.

The term "linker" as used herein refers to a molecule bound to both the protease-disabling moiety and the PAR-1 peptide. Linkers may be amino-acid moieties, peptide moieties, nucleotide moieties, oligonucleotide moieties etc. Contemplated linkers may also serve a further therapeutic purpose, for example, they may be fluorescent, thereby enabling detection of the peptide conjugates carrying them, or they may be a polyethylene glycol (PEG) moiety, further protecting the peptide conjugates carrying them from degradation.

Variants or analogs of the peptide sequences are encompassed by the present invention. A variant/analog according to the present invention retains at least 70%, at least 80% or at least 90% or at least 95%, of the biological activity of the sequence from which it was derived, or to which it is most similar.

A variant as used herein comprises a peptide moiety having at least 80% sequence identity with the peptide Asp-Pro-Arg or any one of the peptides set forth in SEQ ID NO:1 to SEQ ID NO: 17, for example at least 85%, at least 90%, at least 95%, at least 97%, at least 99% sequence identity with the peptide Asp-Pro-Arg or any one of the peptides set forth in SEQ ID NO:1 to SEQ ID NO: 17. Each possibility represents a separate embodiment of the present invention. In some embodiments, said variants may comprise conservative substitutions relative to the amino acid sequence of the peptide moiety corresponding thereto.

Examples of conservative substitutions as considered in the present invention are the substitution of any positive-charge amino-acid (Arg, His, Lys) with any other positive-charge amino-acid; the substitution of any negative-charge amino-acid (Asp, Glu) with any other negative-charge amino-acid; the substitution of any polar-uncharged amino-acid (Ser, Thr, Asn, Gln) with any other polar-uncharged amino-acid; or the substitution of any hydrophobic amino acid (Ala, Ile, Leu, Met, Phe, Trp, Tyr, Val) with any other hydrophobic amino-acid.

Residue positions, which are not identical, may also be composed of peptide analogs, including for example unnatural amino acids or derivatives of such. Analogs typically differ from naturally occurring peptides at one, two or a few positions. Analogs may include unnatural amino acids or modifications of N or C terminal amino acids at one, two or a few positions. Examples of unnatural amino acids, without limiting to, are D-amino acids, alpha, alpha-disubstituted amino acids, N-alkyl amino acids, lactic acid, 4-hydroxyproline, γ-carboxyglutamate, epsilon-N,N,N-tri methyllysine, epsilon-N-acetyllysine, 0-phosphoserine, N-acetylserine, N-formylmethionine, 3-methylhistidine, 5-hydroxylysine, omega-N-methylarginine, and isoaspartic acid.

A peptide conjugate used according to the present invention may be administered systemically, for example, via intravenous (IV) administration or subcutaneous (SC) administration. Each possibility represents a separate embodiment of the present invention. In some embodiments, the peptide conjugate is administered systemically in conjugation with radiation therapy. The radiation therapy may facilitate the penetrance of the peptide conjugate through the blood-brain-barrier (BBB).

A peptide conjugate used according to the present invention may also be administered intra-cranially. A peptide conjugate according to the present invention may also be administered into the central nervous system (CNS) of the subject by intracerebroventricular (ICV) administration. For example, the peptide conjugate may be administered by an intraventricular catheter attached to a reservoir, such as an Ommaya reservoir.

The reservoir may be loaded with a composition comprising the peptide conjugate, and the composition flows through the catheter until the reservoir is emptied, for example, over a period of several days to several weeks, such as over 7 days, 10 days, or two weeks. After the reservoir is emptied, it may be re-loaded for additional treatment session(s), according to the condition of the subject and additional considerations, as may be determined by a clinical practitioner.

In some embodiments, the peptide conjugate is administered directly into the tumor. In other embodiments, the peptide conjugate is administered into an area from which the tumor or a portion thereof has been surgically resected. In additional embodiments, the peptide conjugate is administered into an area surrounding the tumor.

For systemic administration of the peptide, the peptide may be administered once daily to once weekly over a predetermined period of time.

In some embodiments, the peptide conjugate is administered according to the present invention concomitant with TMZ administration, that is, the peptide conjugate is administered during the course of treatment with TMZ. For example, the subject to be treated may receive the peptide conjugate via ICV injections at periodic intervals during the course of treatment with TMZ. As another example, the subject may receive both the peptide conjugate and the TMZ systemically over a predetermined period of time. For systemic administration, the peptide may be administered intravenously or subcutaneously and the TMZ may be administered orally or by intravenous infusions. The subject may optionally also receive radiotherapy during treatment with the peptide conjugate and TMZ.

The peptide conjugate, the TMZ or both may be administered in treatment cycles over a certain period of time, for example 1-12 months, wherein each treatment cycle comprises concomitant administration of the peptide conjugate and temozolomide for a predetermined period of time followed by a period of time in which the peptide conjugate and/or temozolomide are not administered.

In additional embodiments, administration of the peptide conjugate is continued after TMZ treatment is ceased. In other embodiments, administration of the peptide conjugate is ceased before TMZ treatment is ceased.

In some embodiments, the peptide conjugate and TMZ are administered concomitantly. In other embodiments, the peptide conjugate and TMZ are administered sequentially.

In some embodiments, the peptide conjugate is administered by ICV administration and the TMZ is administered orally. In other embodiments, the peptide conjugate is administered by ICV administration and the TMZ is administered by intravenous infusion.

A pharmaceutical composition comprising the peptide conjugate typically comprises a pharmaceutically acceptable carrier, such as water/aqueous solution The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1—Inhibition of Glioma Cell Proliferation

The following experiment tested the effect of the chemotherapeutic drug temozolomide ("TMZ") in combination with the peptide conjugate Tosyl-ATLDPR-chloromethylketone (tosyl-SEQ ID NO: 3-CMK) on the proliferation of glioma cells. The peptide conjugate contains 6 amino acids from the N-terminus of PAR-1: ATLDPR (SEQ ID NO: 3), and is denoted herein as "SIXAC".

Figure 1:
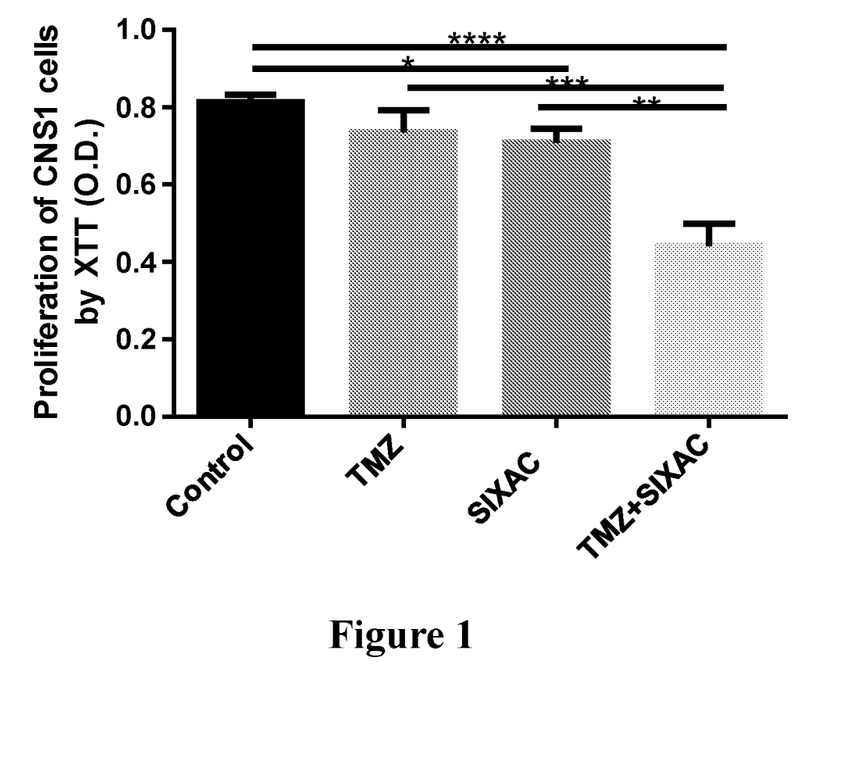
FIG. 1. Effect of temozolomide ("TMZ") and Tosyl-ATLDPR-chloromethylketone (tosyl-SEQ ID NO: 3-chloromethylketone) ("SIXAC") on proliferation of CNS-1 cells in vitro.

In particular, CNS-1 glioma cell line (rat) was treated with either TMZ (500 μM), SIXAC (10 μM) or a combination of TMZ (500 μM) and SIXAC (10 μM) for 72 hours. Proliferation was measured by means of XTT in comparison to non-treated cells (control). The results are shown in FIG. 1.

As can be seen in the figure, a prominent reduction of cell proliferation was obtained by the combination of TMZ and SIXAC compared to control non-treated cells. The reduction was significantly better than the reduction obtained by SIXAC alone. TMZ alone had no significant effect on the proliferation of the CNS-1 cells (*<0.05, <0.01, *<0.001, ****<0.0001).

The results show that a major inhibitory effect on proliferation of glioma cells can be achieved with a combination of TMZ and SIXAC, at concentrations in which each treatment alone is ineffective or results only in a minor effect.

Example 2—Effect on Survival in an Animal Model of GBM

CNS-1 cells ($5 \times 10^7$ cells) were injected using stereotactic methods into the parietal cortex of rats (n=20, 16 rats survived the surgery).

Five days later (Day 5) the brains of the rats that survived the surgery were examined by MRI and the tumors scored on a scale of 1-3. For each rat, a catheter was placed in the brain tumor and attached to an osmotic pump (Alzet®) releasing one of the following treatments (0.50 h, for 14 days): TMZ 2 mg/rat (n=7), or TMZ 2 mg/rat and SIXAC 6.9 μg/rat (20 μg/kg/day) (n=7) (TMZ was dissolved in saline and 0.1M acetate buffer pH5) (50:50 v/v ratio).

The groups were monitored daily for survival until Day 25. The results are summarized in FIGS. 2A+B.

Figure 2A:
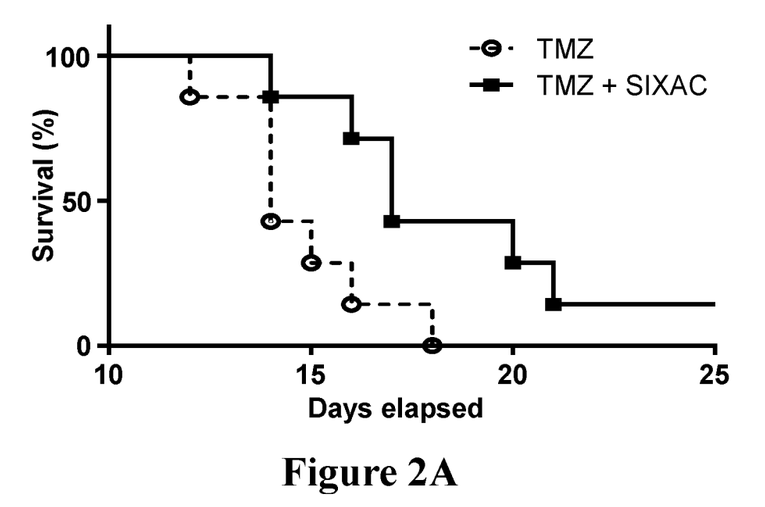
FIG. 2. Effect of temozolomide ("TMZ") and Tosyl-ATLDPR-chloromethylketone (tosyl-SEQ ID NO: 3-chloromethylketone) ("SIXAC") on survival in a rat model of GBM.
Figure 2B:
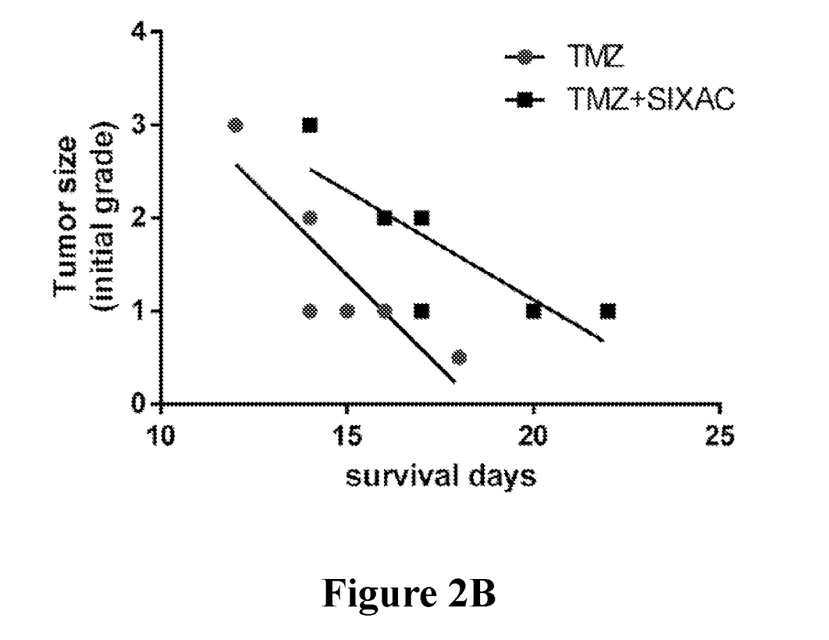

FIG. 2A shows the survival percentage in each group throughout the study period. As can be seen in the figure, the survival in the group that received the combined treatment of TMZ and SIXAC was significantly increased compared to the survival in the group which received TMZ alone (Log-rank (Mantel-Cox) test P=0.0204; Gehan-Breslow-Wilcoxon test P=0.0277), with one rat surviving longer than the study period (this rat was sacrificed after 18 weeks (=at day 126)). Median survival was 18.5 days in the combined treatment group vs. 14 days in the TMZ group.

FIG. 2B shows the survival of rats in each group according to their initial tumor grade (as determined by the MRI scan on Day 1, prior to any treatment). As can be seen in the figure, in both groups, rats with lower grade tumors survived better than rats with higher grade tumors. Rats in the combined treatment group showed better survival for all grades compared to rats that received TMZ alone.

To conclude, the results show that a significant improvement in survival can be achieved with a combination of TMZ and SIXAC in a GBM animal model, even for high grade tumors.

Example 3—Effect of SIXAC and TMZ on PAR-1 Pathway in Glioma Cells

The following experiment examined a possible mechanism underlying the synergy observed between SIXAC and TMZ. More particularly, the expression of two proteins, PAR-1 and phosphorylated extracellular signal-regulated kinase (pERK), was examined in glioma cells incubated with TMZ, SIXAC or a combination of TMZ+SIXAC.

Methods

Cell Culture

CNS-1 rat glioma cells were grown in Dulbecco's modified Eagle's medium (DMEM; Bet Haemek, Biological Industries, Israel) supplemented with 10% fetal bovine serum (Bet Haemek, Biological Industries, Israel) and 1% penicillin and streptomycin in a 5% CO2-humidified atmosphere.

Western Blot Analysis

CNS-1 cells were seeded and incubated for 24 h. Then the medium was replaced by FCS-free medium for additional 24 h. Next, the cells were treated for 24 h with SIXAC (10 μM), TMZ (500 μM), a combination of TMZ (500 μM) and SIXAC (10 μM) or a FCS-free medium (containing 0.2%

DMSO) which was used as a control (n=4 for each treatment group). The cells were then washed with ice-cold PBS and lysed in RIPA buffer (containing in mM: 50 TRIS HCl pH 8, 150 NaCl, 1% NP-40, 0.5% sodium deoxycholate, and 0.1% SDS), a protease inhibitor cocktail (Merck Millipore 539134, 1:100), 0.1 mM sodium orthovanadate and 2 mM PMSF. The cells were scraped, collected and centrifuged (16,000 g×20 min) at 4° C. The supernatants were collected, and protein concentration was determined by means of a bicinchoninic acid (BCA) assay. Each sample (20 µg) was separated by SDS-polyacrylamide gel electrophoresis. The proteins were transferred onto nitrocellulose membranes. Membranes were incubated with mouse anti-phosphorylated Extracellular signal-Regulated Kinase (pERK) antibody (1:10,000, M8159, Sigma) or rabbit anti PAR-1 antibody (1:500, abcam 32611) for 1.5 h at room temperature (RT) and washed with TRIS-buffered saline and 0.1% Tween 20 (TBST). Membranes were then incubated at RT with horseradish peroxidase-conjugated goat anti-mouse or rabbit antibody (1:10,000, Jackson Immunoresearch Laboratories). Protein bands were detected by a peroxidase-based enhanced chemiluminescence (ECL) method. Analysis of the protein band density was performed with ImageJ software.

Results

Figure 3A:
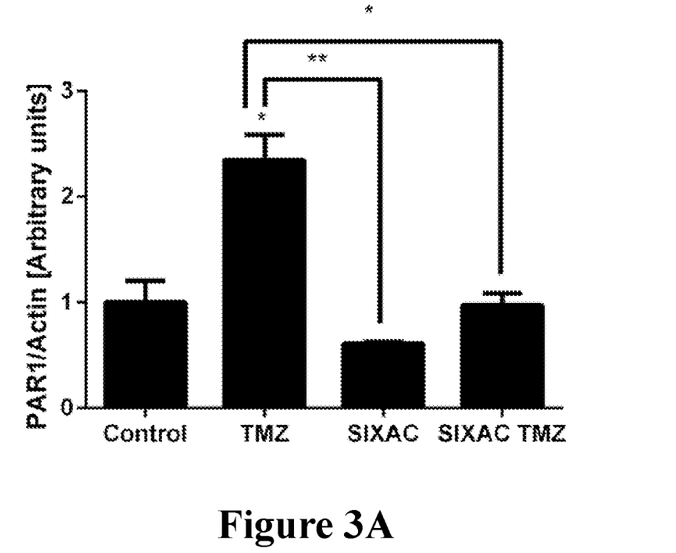
FIG. 3. Levels of PAR1 (A) and pERK (B) in CNS1 rat glioma cells following treatment with TMZ, SIXAC or TMZ+SIXAC. Medium only served as the control.
Figure 3B:
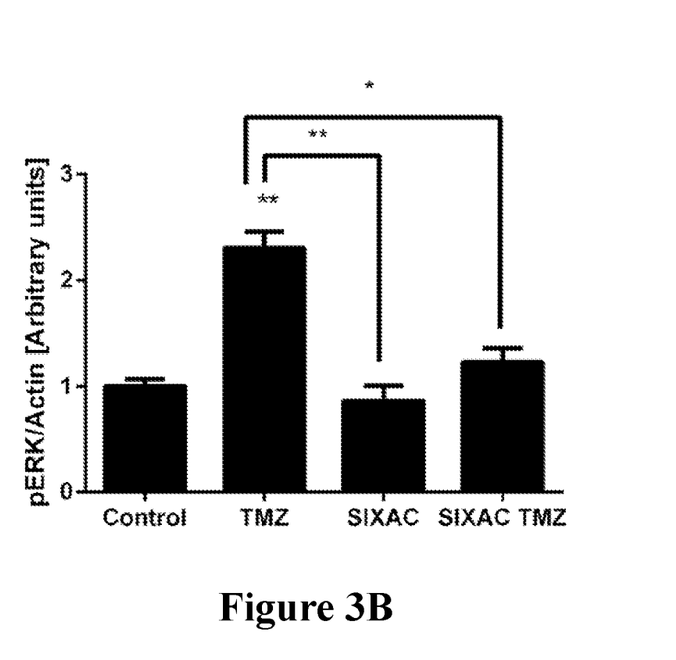

The results are summarized in FIGS. 3A-B. TMZ treatment for 24 h caused a significant increase in PAR1 and pERK expression in CNS1 rat glioma cells. This increase was prevented when TMZ was applied together with SIXAC. SIXAC by itself did not cause any significant change in neither PAR1 nor pERK levels (*<0.05, **<0.01). Without wishing to be bound by any particular theory of a mechanism of action, this increase in the levels of PAR-1 and pERK may indicate that TMZ causes a certain feedback process involving PAR-1 pathway induction, which renders the cells more sensitive to the inhibitory effect of SIXAC compared to their sensitivity when SIXAC is administered alone.

Example 4—Effect of SIXAC and TMZ on Glioma Cell Migration

Methods

Cell Culture

C6 rat glioma cells were grown in Dulbecco's modified Eagle's medium (DMEM; Bet Haemek, Biological Industries, Israel) supplemented with 10% fetal bovine serum (Bet Haemek, Biological Industries, Israel) and 1% penicillin and streptomycin in a 5% $CO_2$-humidified atmosphere.

Scratch (Wound Healing) Assay

The effect of TMZ and SIXAC on the coordinated movement of C6 glioma cells was evaluated using a wound healing assay. The cells were seeded in 24-well plates at a density of 5×10^4 cells/well. Cells were cultured in FCS-free medium for 24 h. A wound was established by scraping using 10 µl pipette tip. Cells were washed twice with warm PBS and then fresh FCS-free medium was added, containing SIXAC (1 µM), TMZ (100 µM) or a combination of SIXAC and TMZ. Wells with FCS-free medium only or FCS-free medium+DMSO 0.2% were used as controls (marked as "control" and "control+DMSO") Image acquisition of wound gap closure (%) was carried out following 4 h of incubation using a Nikon Eclipse microscope Images were analyzed using Fiji software.

Results

Figure 4A:
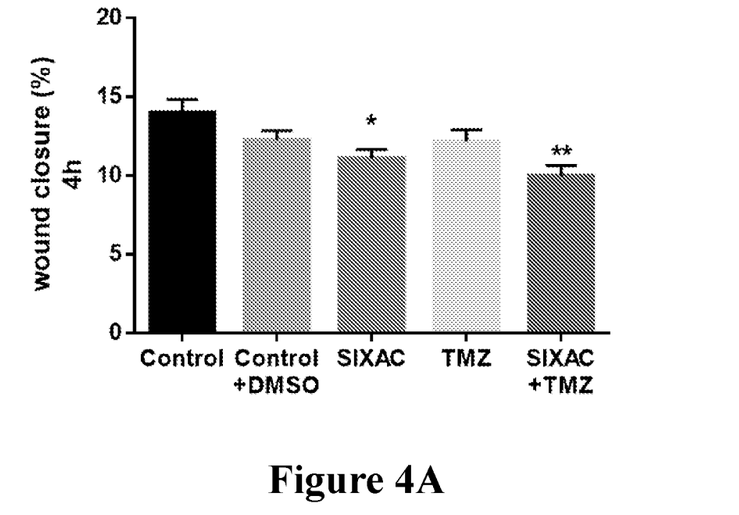
FIG. 4. Wound closure rate in C6 rat glioma cells following treatment with TMZ, SIXAC or TMZ+SIXAC. Medium/medium+DMSO served as controls. (A) Wound-closure percentage (B) A representative image of scratched cultures before and after treatment.
Figure 4B:
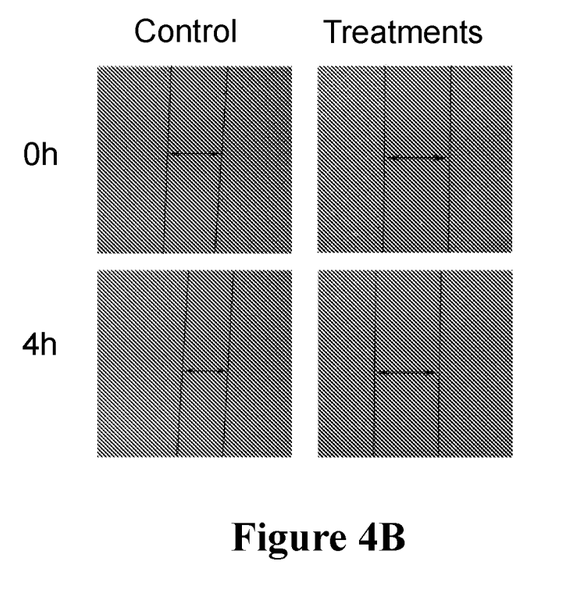

The results are summarized in FIGS. 4A-B. SIXAC but not TMZ was found to significantly decrease the wound-closure percentage. A combination of SIXAC and TMZ was particularly effective and reduced the wound-closure percentage even further, significantly more than SIXAC alone. The results indicate effective synergistic inhibition of cell migration by the combination.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A method for treating malignant glioma in a subject in need thereof, the method comprising administering to the subject a peptide conjugate having the following general formula: α-amino protecting moiety-PAR-1 peptide-protease-disabling moiety, wherein the PAR-1 peptide is selected from the group consisting of Asp-Pro-Arg and SEQ ID NOs: 1-17, and administering temozolomide the said subject.

2. The method of claim 1, wherein the PAR-1 peptide is selected from the group consisting of Asp-Pro-Arg and SEQ ID NOs: 1-4.

3. The method of claim 1, wherein the PAR-1 peptide is Ala-Thr-Leu-Asp-Pro-Arg (SEQ ID NO: 3).

4. The method of claim 1, wherein the α-amino protecting moiety is tosyl or a derivative thereof.

5. The method of claim 1, wherein the protease-disabling moiety is chloromethylketone or a derivative thereof.

6. The method of claim 1, wherein the peptide conjugate is: tosyl-Ala-Thr-Leu-Asp-Pro-Arg-chloromethylketone (tosyl-SEQ ID NO: 3-chloromethylketone).

7. The method of claim 6, wherein the peptide conjugate is administered into the central nervous system (CNS) of the subject.

8. The method of claim 7, wherein the peptide conjugate is administered by intracerebroventricular (ICV) administration.

9. The method of claim 1, wherein the peptide conjugate is administered systemically.

10. The method of claim 1, wherein the peptide conjugate is administered once daily to once weekly.

11. The method of claim 1, wherein the temozolomide is administered orally.

12. The method of claim 1, wherein the temozolomide is administered by intravenous infusion.

13. The method of claim 1, wherein the subject is further receiving radiotherapy.

14. The method of claim 1, wherein the peptide conjugate and the temozolomide are administered concomitantly in a plurality of treatment cycles over a period of time of 1-12 months, wherein each treatment cycle comprises concomitant administration of the peptide conjugate and temozolomide for a predetermined period of time followed by a period of time in which the peptide conjugate and temozolomide are not administered.

15. The method of claim 1, wherein the temozolomide is administered in treatment cycles, each comprising a predetermined period of time in which the temozolomide is administered followed by a period of time in which the temozolomide is not administered, and the peptide conjugate is administered continuously.

16. The method of claim 1, wherein the peptide conjugate is administered directly into the tumor.

17. The method of claim 1, wherein the peptide conjugate is administered into an area from which the tumor or a portion thereof has been surgically resected.

18. The method of claim 1, wherein the peptide conjugate is administered into an area surrounding the tumor.

19. The method of claim 1, wherein the malignant glioma is glioblastoma.

20. The method of claim 19, wherein the glioma is glioblastoma multiforme.

\* \* \* \* \*

SEQUENCE LISTING

<160> NUMBER OF SEQ ID NOS: 17

<210> SEQ ID NO 1
<211> LENGTH: 4
<212> TYPE: PRT
<213> ORGANISM: Artificial Sequence
<220> FEATURE:
<223> OTHER INFORMATION: Peptide

<400> SEQUENCE: 1

Leu Asp Pro Arg
1

<210> SEQ ID NO 2
<211> LENGTH: 5
<212> TYPE: PRT
<213> ORGANISM: Artificial Sequence
<220> FEATURE:
<223> OTHER INFORMATION: Peptide

```
<400> SEQUENCE: 2

Thr Leu Asp Pro Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Peptide

<400> SEQUENCE: 3

Ala Thr Leu Asp Pro Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Peptide

<400> SEQUENCE: 4

Asn Ala Thr Leu Asp Pro Arg
1               5

<210> SEQ ID NO 5
<211> LENGTH: 8
<212> TYPE: PRT
<213> ORGANISM: Artificial Sequence
<220> FEATURE:
<223> OTHER INFORMATION: Peptide

<400> SEQUENCE: 5

Thr Asn Ala Thr Leu Asp Pro Arg
1               5

<210> SEQ ID NO 6
<211> LENGTH: 9
<212> TYPE: PRT
<213> ORGANISM: Artificial Sequence
<220> FEATURE:
<223> OTHER INFORMATION: Peptide

<400> SEQUENCE: 6

Ala Thr Asn Ala Thr Leu Asp Pro Arg
1               5

<210> SEQ ID NO 7
<211> LENGTH: 10
<212> TYPE: PRT
<213> ORGANISM: Artificial Sequence
<220> FEATURE:
<223> OTHER INFORMATION: Peptide

<400> SEQUENCE: 7

Lys Ala Thr Asn Ala Thr Leu Asp Pro Arg
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Peptide
```

```
<400> SEQUENCE: 8

Ser Lys Ala Thr Asn Ala Thr Leu Asp Pro Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Peptide

<400> SEQUENCE: 9

Glu Ser Lys Ala Thr Asn Ala Thr Leu Asp Pro Arg
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Peptide

<400> SEQUENCE: 10

Pro Glu Ser Lys Ala Thr Asn Ala Thr Leu Asp Pro Arg
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Peptide

<400> SEQUENCE: 11

Arg Pro Glu Ser Lys Ala Thr Asn Ala Thr Leu Asp Pro Arg
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Peptide

<400> SEQUENCE: 12

Arg Arg Pro Glu Ser Lys Ala Thr Asn Ala Thr Leu Asp Pro Arg
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Peptide

<400> SEQUENCE: 13

Ala Arg Arg Pro Glu Ser Lys Ala Thr Asn Ala Thr Leu Asp Pro Arg
1               5                   10                  15

<210> SEQ ID NO 14
<211> LENGTH: 17
<212> TYPE: PRT
<213> ORGANISM: Artificial Sequence
<220> FEATURE:
<223> OTHER INFORMATION: Peptide
```

```
<400> SEQUENCE: 14

Arg Ala Arg Arg Pro Glu Ser Lys Ala Thr Asn Ala Thr Leu Asp Pro
1               5                   10                  15

Arg

<210> SEQ ID NO 15
<211> LENGTH: 18
<212> TYPE: PRT
<213> ORGANISM: Artificial Sequence
<220> FEATURE:
<223> OTHER INFORMATION: Peptide

<400> SEQUENCE: 15

Thr Arg Ala Arg Arg Pro Glu Ser Lys Ala Thr Asn Ala Thr Leu Asp
1               5                   10                  15

Pro Arg

<210> SEQ ID NO 16
<211> LENGTH: 19
<212> TYPE: PRT
<213> ORGANISM: Artificial Sequence
<220> FEATURE:
<223> OTHER INFORMATION: Peptide

<400> SEQUENCE: 16

Arg Thr Arg Ala Arg Arg Pro Glu Ser Lys Ala Thr Asn Ala Thr Leu
1               5                   10                  15

Asp Pro Arg

<210> SEQ ID NO 17
<211> LENGTH: 20
<212> TYPE: PRT
<213> ORGANISM: Artificial Sequence
<220> FEATURE:
<223> OTHER INFORMATION: Peptide

<400> SEQUENCE: 17

Ala Arg Thr Arg Ala Arg Arg Pro Glu Ser Lys Ala Thr Asn Ala Thr
1               5                   10                  15

Leu Asp Pro Arg
            20
```